United States Patent [19]

Christlieb

[11] Patent Number: 5,113,858
[45] Date of Patent: May 19, 1992

[54] METHOD FOR CONTROL OF OUTPUT OF CARDIOMYOSTIMULATOR

[75] Inventor: Ignacio Y. Christlieb, Pittsburgh, Pa.

[73] Assignee: Allegheny-Singer Research Institute, Pittsburgh, Pa.

[21] Appl. No.: 508,845

[22] Filed: Apr. 12, 1990

[51] Int. Cl.⁵ .............................................. A61N 1/08
[52] U.S. Cl. ................................................ 128/419 P
[58] Field of Search ..................... 600/15; 128/419 PS, 128/419 PG

[56] References Cited

U.S. PATENT DOCUMENTS

| | | | |
|---|---|---|---|
| 3,195,540 | 7/1965 | Waller | 128/419 PT |
| 3,782,368 | 1/1974 | Reibold | 128/687 |
| 4,735,204 | 4/1988 | Sussman et al. | 128/419 |

FOREIGN PATENT DOCUMENTS 1082752  9/1967  United Kingdom ............ 128/419 P

Primary Examiner—William E. Kamm
Attorney, Agent, or Firm—Webb, Burden, Ziesenheim & Webb

[57] ABSTRACT

Method and apparatus for controlling the output of a cardiomyostimulator comprising a magnet of sufficient intensity to interrupt an output signal of a cardiomyostimulator when placed externally over the abdomen of a patient in whom a cardiomyostimulator has been implanted in close proximity to the cardiomyostimulator, and a belt member for removably securing the magnet over the patient's abdomen.

34 Claims, 2 Drawing Sheets

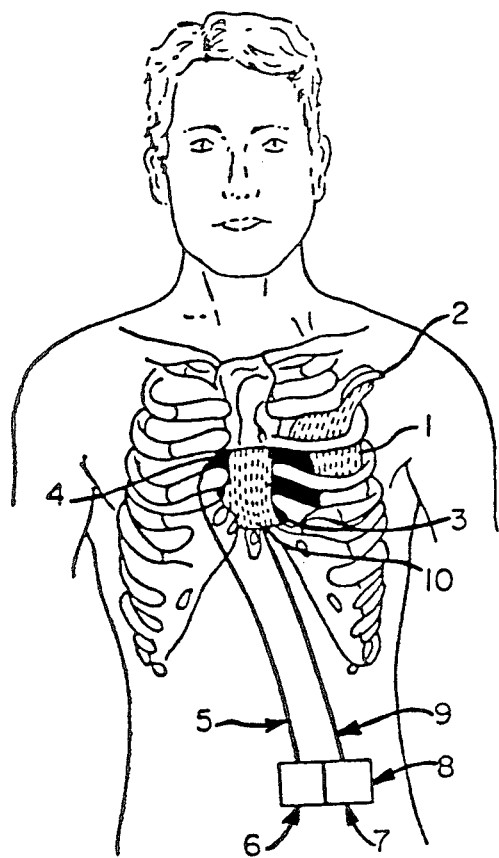
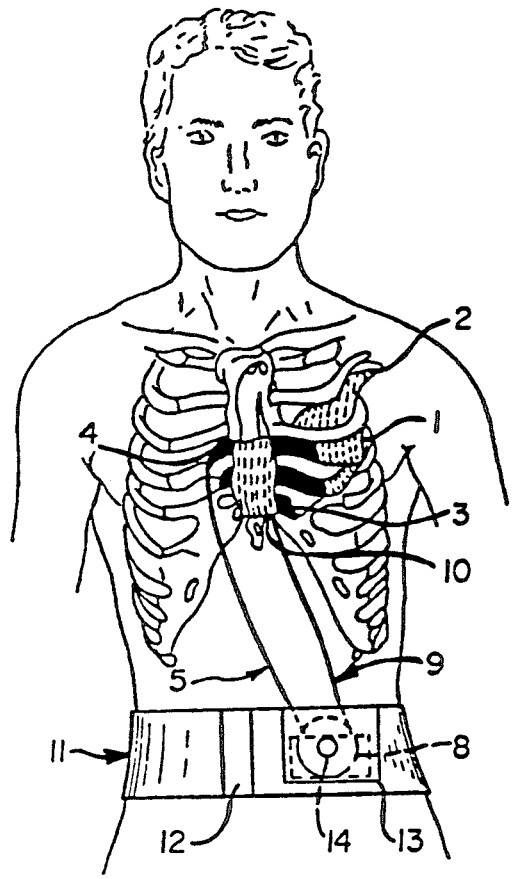
FIG. 1
FIG. 2
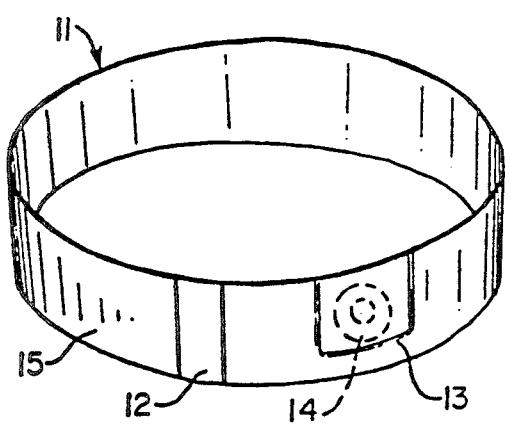
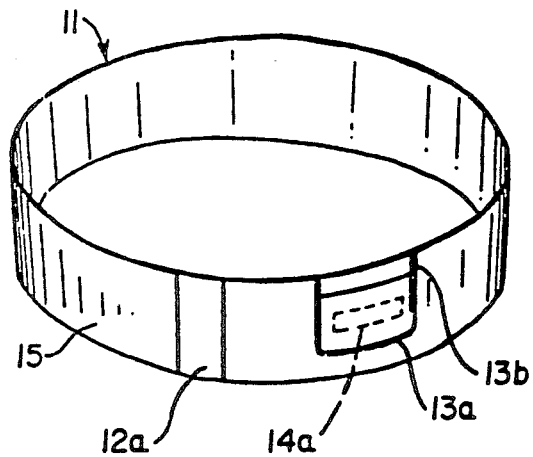
FIG. 3A
FIG. 3B

METHOD FOR CONTROL OF OUTPUT OF CARDIOMYOSTIMULATOR

BACKGROUND OF THE INVENTION

1. Field Of The Invention

The invention pertains to an apparatus for control of the output of a cardiomyostimulator and the method for using it.

2. Description Of The Prior Art

A surgical procedure known as Muscle Flap Heart Function Augmentation was pioneered by George Magovern, M. D. This procedure is also known as a cardiomyoplasty and is disclosed and claimed in U.S. Pat. No. 4,791,911 issued Dec. 20,1988 to George Magovern.

In this surgical procedure, the latissimus dorsi is partially dissected from its location in the back while leaving the neurovascular bundle intact. The blood supply and nerve tissues are not severed and remain intact to nourish and excite the muscle. The dissected muscle (also known as and hereinafter referred to as a "muscle flap") is translocated and is passed into the thorax through a rib resection in the axilla. After appropriate midsternotomy, cardiopulmonary bypass etc., the muscle flap is used as a graft muscle in the reconstruction of the cardiac muscle.

For several days postoperatively the muscle flap is permitted to heal before contractions (which might otherwise tear the sutures) are initiated. Subsequently, a protocol of suitable pacing of the muscle flap with a pulsed stimulus is initiated which enables the muscle flap to contribute to the overall cardiac function.

It has been found that the muscle flap can be made to beat in rhythm with the heart in response to signals generated by a type of implantable pulse generator (IPG), as hereinafter described and generically known as a cardiomyostimulator, although it may be known by other names or terms as well. Further, as used in this application, the term cardiomyostimulator is defined to include one or more devices, elements or any combination or configuration that is implanted for the purpose of stimulating graft tissue to augment the cardiac or circulatory function, including but not limited to co-pulsating and counter-pulsating devices. One example of such a device is Model SP1005, marketed under the trademark Cardio-Myostimulator ™ available from Medtronic ®, Inc., of Minneapolis, Minn.

The cardiomyostimulator is both a "receiving" unit and a "sending" unit. As the heart muscle begins its contraction, a sensor which is associated with the heart, senses occurrence of electrical impulses generated by the heart muscle (specifically the depolarization of the atria or ventricle), which immediately precedes and initiates systolic contraction and the sensor in turn generates a signal which is "received" by the cardiomyostimulator. The cardiomyostimulator in turn transfers that signal to the sending unit portion. The muscular channel, or sending unit portion of the cardiomyostimulator, generates one or more pulses either individually or in a burst pattern, and through electrodes implanted in the muscle flap causes the muscle flap to contract in synchrony with the left ventricle to which it is attached, assisting the left ventricle and increasing its output of blood to the body. The cardiomyostimulator is usually implanted in the upper left portion of the abdominal wall.

It has been found by those skilled in the art that over a period of time, the endurance of the muscle flap can be increased thereby causing the muscle tissue of the back to take on more of the characteristics of heart muscle.

Further, it has been found by those skilled in the art (at Allegheny General Hospital of Pittsburgh, Pa. and the Allegheny Singer Research Institute of Pittsburgh, Pa.) that the muscle flap needs to be conditioned so that it can function as heart muscle with contractions stimulated by a signal generated by the cardiomyostimulator, otherwise the muscle flap suffers from fatigue.

Although the process of muscle fatigue is variously defined by those skilled in the medical profession, one definition applicable to the present invention is that fatigue is the process by which a muscle uses energy (while working) at a rate faster than it is replaced (when the muscle rests). For example, typically non-cardiac muscle can work/rest in a ratio of approximately 30%/70% without fatigue. Cardiac muscle by contrast has a work/rest (rest being defined as the period between contraction) ratio estimated at 70%/30%.

Thus it has been found that the muscle flap must be conditioned in order to increase its work ratio to a maximum while minimizing its rest ratio. In light of the foregoing, it was found by those skilled in the art as referenced above, that initiating pulsed stimulus of the muscle flap too soon after surgery (with a stimulus causing strong contraction of the muscle flap) without periods of rest, causes damage to the muscle flap from fatigue by depletion of muscle energy that is not replenished, and ultimately atrophy of the overstimulated muscle flap tissue.

Two schools of thought and two corresponding methods have been developed to overcome this problem of fatigue. One school of thought can be briefly categorized as using a "full strength/ patterned episodes of pulsed stimulus and rest" method. The second school of thought can be briefly categorized as using an "increasing strength/constantly pulsed stimulus" method.

With the first method, for a predetermined healing period after the cardiomyoplasty, the muscle flap is permitted complete rest with no stimulation. At the end of this initial rest period, the muscle flap is subjected to a "training period". The training period is defined as a period of time during which the muscle flap is gradually conditioned for endurance so that it can beat in rhythm with the heart. This training period involves a training schedule which is quite similar to the training schedule an athlete such as a marathon runner would follow. The training schedule consists of alternating episodes of rest and exercise. During the exercise episodes, the muscle flap is stimulated at a sufficient level so as to cause contraction in synchrony with the patient's heart. The exercise episodes continue in ever-increasing duration until the muscle flap has been conditioned and toned to withstand the strain of continuous pulsed stimulation. It is believed by those skilled in the art that if the muscle flap is not continuously paced during the training period, that the skeletal muscle fibers will transform and develop the capacity for contracting in synchrony with the original heart muscle more effectively, for longer periods of time and with less risk of skeletal muscle atrophy.

The second method involves training the muscle flap to contract in synchrony with the heart without any periods of rest. This method begins by supplying a very low level of pulsed stimulus in synchrony with the beating of the patient's heart early during the muscle flap training period. The pulsed stimulus is continuously supplied and progressively increased in intensity until the muscle flap has been conditioned to accept the level of pulsed stimulus which will enable it to contract in synchrony with the patient's heart without fatiguing, i.e. the muscle flap is fully conditioned.

Both of these methods suffer from the limitation that under either method of conditioning and training of the muscle flap, it is necessary for the patient to remain in a specialized health care facility for management of stimulation problems and/or return at extremely frequent intervals in order to effect changes in the duration or intensity of the stimulating signals. This results in severe inconvenience and increased health care costs to the patient in the form of longer hospital stays and inability to lead a normal life-style due to the need to return to the hospital on a daily or nearly daily basis during the "training period".

Regardless of the training method followed, the cardiomyoplasty procedure leads to a need for temporary interruption of the pulsed stimulus for two distinct purposes:

1. Patients often develop a fear or apprehension of an implanted device that causes contraction of tissue which is beyond the patient's control. The patient needs to have a mechanism for controlling the output of the cardiomyostimulator.

2. When the patient is seen by another physician for emergency or other reasons, and that physician does not have access to a device capable of controlling the cardiomyostimulator's output, the physician is helpless to temporarily interrupt the output of the cardiomyostimulator in order to test questionable functioning of the stimulator, questionable response from the muscle flap, or for evaluation of the patient's own heart or heart function (such as by electro-and echo-cardiograms) in the absence of the contractions of the translocated muscle.

Thus, there has arisen in the art the need for a simple, reliable and effective method and device for controlling the output of a cardiomyostimulator which is available to or for patients at all times, and which, while under the direction and supervision of a physician, can be used to control the stimulating device instantly from any location anywhere in the world.

SUMMARY OF THE INVENTION

It is an object of the present invention to overcome the above-described limitations by providing a device and method capable of controlling the output of a cardiomyostimulator.

These and other objects are attained by the present invention which provides a method and a device for controlling the output of a cardiomyostimulator comprising a magnet of sufficient intensity to interrupt an output signal of a cardiomyostimulator when placed externally over the abdomen in close proximity to said cardiomyostimulator of a patient in whom said cardiomyostimulator has been implanted, and a means for removably securing the magnet over the abdomen.

BRIEF DESCRIPTION OF THE DRAWINGS

FIG. 1 is a diagrammatic view of the ventral thorax of the human body showing the placement of the cardiomyostimulator with sensing and stimulating leads;

FIG. 2 is a diagrammatic view of the ventral thorax of the human body showing the placement of the magnetic belt of the present invention;

FIG. 3A is a perspective view of the magnetic belt of the present invention showing the use of a circular magnet;

FIG. 3B is a perspective view of the magnetic belt of the present invention showing the use of a bar magnet removably mounted in a resealable pouch.

DESCRIPTION OF THE PREFERRED EMBODIMENTS

Figure 4:
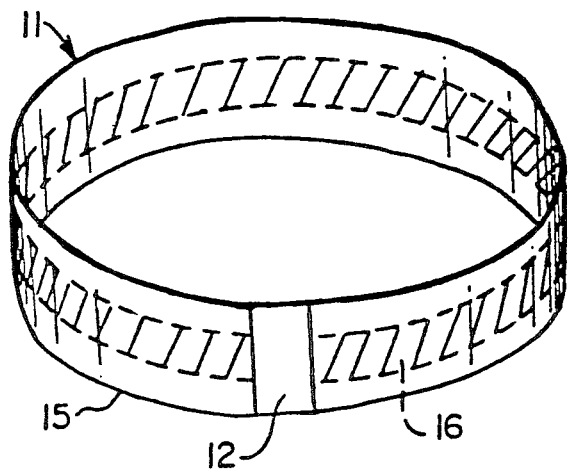
FIG. 4 is a perspective view of the magnetic belt of the present invention showing the use of a magnetic bunting material around the circumference of the magnetic belt.

According to the present invention, a method and device are provided for use in conjunction with the surgical procedure known as cardiomyoplasty, which are used to turn off the stimulating device for training, safety, testing or other purposes.

The device of the present invention comprises:

a magnet of sufficient intensity to interrupt an output signal of a cardiomyostimulator when placed externally over the abdomen in close proximity to said cardiomyostimulator of a patient in whom said cardiomyostimulator has been implanted, and a means for removably securing the magnet over the abdomen.

To the extent necessary for a full understanding of the present invention, the teachings of U.S. Pat. No. 4,791,911 are incorporated herein by reference.

Referring now to FIG. 1, the latissimus dorsi autograft or muscle flap 1 is shown in place and wrapped around the heart 3 to which it is sutured. Although truncated for purposes of illustration, the neurovascular bundle 2 maintains the same neurovascular interconnections it has prior to the cardiac reconstruction procedure as described in more detail in U.S. Pat. No. 4,791,911.

Sensor 4, not shown, is implanted in either the atria or ventricle of heart 3 and is capable of sensing the depolarization of the heart muscle that initiates the systolic contraction of heart 3. Although a detailed discussion of the sensor 4 is not required for an understanding of the present invention, typical sensors are capable of measuring the summed voltage rise across heart muscle which precedes systolic contraction. Typically, before contraction, there exists a voltage of approximately −70 to −90 mv as measured across the cell membrane. During the depolarization process which occurs during contraction, the voltage rises, typically reaching a final voltage of approximately +20 to +30 mv as measured across the heart muscle cellular membrane.

As indicated, cardiomyostimulator 8 (shown diagrammatically) is both a "receiving unit" and a "sending unit". Thus sensor 4 sends its signal via signal transfer means 5, to the signal receiving portion 6 of cardiomyostimulator 8. The cardiomyostimulator 8, in turn, internally interprets and transfers that signal to its sending unit portion 7. The myostimulator, or sending unit portion 7 of cardiomyostimulator 8, generates a stimulus signal which is transferred by signal transfer means 9 to stimulus electrode 10 (not shown), causing muscle flap 1 to contract in rhythm with the beating of the heart, thereby assisting the heart and increasing the blood supply to the entire body.

As disclosed in U.S. Pat. No. 4,791,911, in one embodiment for sensing and stimulation of the muscle flap, a bipolar A-V-DDD universal pacer is applied to the cardiac wall. Two epicardial type screw-on type leads associated with the cardiac pacer are placed on the latissimus dorsi, with the first near the neurovascular bundle and the second distally over the muscle as it lay on the repair.

The cardiomyostimulator 8 is usually implanted in the upper left portion of the abdominal wall as shown in FIG. 1.

Referring now to FIG. 2, magnetic belt 11 of the present invention is shown being worn by a patient over the abdominal wall.

Magnetic belt 11, comprises a magnet 14 of sufficient magnetic intensity to interrupt an output signal of a cardiomyostimulator 8 (shown in phantom) when placed externally over the abdomen in close proximity to cardiomyostimulator 8 which has been implanted in the abdominal wall of a patient. For purposes of illustration, magnet 14 has been depicted as a circular or doughnut magnet, although numerous magnet configurations are envisioned with the present invention, as discussed below.

Magnetic belt 11 also comprises a magnet retaining means 13, which may alternatively either permanently or temporarily affix magnet 14 to belt 11, as is discussed further below.

Magnetic belt 11 further comprises a means 12 for removably securing magnet 14 over the abdomen. Means 12 for removably securing magnet 14 over the abdomen is illustrated as utilizing a hook and loop design for purposes of illustration, although numerous configurations are envisioned with the present invention as discussed below.

The magnet 14 of the present invention may take any of numerous possible forms. Examples include but are not limited to bar magnets, circular or "doughnut" magnets, "horse shoe" magnets, and flexible magnetic strips and sheets.

The critical aspect of magnet 14 is that it must possess sufficient magnetic properties to temporarily interrupt the output signal of the cardiomyostimulator 8 when placed externally over the abdomen wherein the cardiomyostimulator 8 is implanted. One example of such a magnet is Model 7450 Pulse Generator Magnet available from Medtronic ®, Inc., of Minneapolis, Minn. The Model 7450 magnet is a circular magnet and has a field strength of 90 minimum measured at 1.5 inches from the magnet surface. The magnet preferably has a field strength of at least 15 pounds per foot pull strength measured on bare metal at zero air gap regardless of magnetization pattern.

It is important to note that in a preferred embodiment the magnetic field strength of magnet 14 is only strong enough to reliably interrupt the output signal of cardiomyostimulator 8, and is no stronger. As will be apparent from the following discussion, several devices, including neural stimulators and cardiac pacemakers can be sensitive to magnetic fields. Therefore, it is desirable to utilize a magnet of limited field strength so that it will reliably interrupt the cardiomyostimulator output, without affecting other magnet-sensitive devices which may be used by or near a patient.

It is not possible to ascribe one given value for the field strength, as the field strength must necessarily vary with several factors, including but not limited to, the thickness of clothing, the thickness of the fat layer within the abdominal cavity of the wearer and the sensitivity of the cardiomyostimulator to interruption of its output signal.

It should be noted that the use of magnets with radio frequency pulse generating devices is known in the art, however their use has been heretofore limited to two very different functions, namely use with neural stimulators and use with cardiac pacemakers.

When a magnet is used with a type of implantable pulse generating device (IPG) known as a neural stimulator the magnet is used as a "magnetic switch" to alternatively switch the output of the neural stimulator either "on" or "off". In this capacity, the magnet is placed on the skin directly over the implant site of the neural stimulator and upon removal the circuit of the neural stimulator is "switched", i.e. if activated it is deactivated or if deactivated it is activated. Neural stimulators are typically used as pain blocking devices and generate electrical pulses which interrupt pain signals generated by the body, thereby relieving the sensation of pain that is felt by the patient. The use of the magnet in the present invention differs from this use, in that the magnet of the present invention is not a "switch", but is more accurately termed a "magnetic interrupter" device. The advantage of this use of the magnet is that there is not the slightest question as to whether with the removal of the magnet the stimulating device has been enabled or disabled, which would otherwise lead to confusion of the patient with potentially undesirable results. With the magnet of the present invention, there is one, and only one function, to wit: as long as the magnet is placed over the pulse generating device, the output signal of the cardiomyostimulator is "interrupted" and the muscle flap is not stimulated. Upon removal of the magnet from contact with the abdomen, the cardiomyostimulator unquestionably resumes programmed stimulation of the muscle flap.

Under the second prior art use of magnets with IPGs, a magnet is known to be used with cardiac pacemakers. The magnet is used with the cardiac pacemaker to either switch the cardiac pacemaker to a testing program in order to evaluate the pacemaker, or to install a completely new program in the cardiac pacemaker to, for instance, cause the cardiac pacemaker to generate pulses at a different rate. Clearly, as indicated above, this use also differs from the use of the magnet in the present invention as a "magnetic interrupter" to completely eliminate the output of the cardiomyostimulator when the magnet is placed in close proximity to the cardiomyostimulator.

The means for removably securing the magnet over the abdomen of a patient in whom the cardiomyostimulator has been implanted may take several forms.

In one embodiment of the magnetic belt 11 of the present invention, as depicted in FIG. 3A, an adjustable belt-like material 15 is designed with a magnet retaining means 13 for retaining a bar or doughnut magnet on said belt-like material 15. For purposes of illustration, a doughnut magnet 14 is depicted in phantom in FIG. 3A, although it is envisioned with the present invention that any type of magnet can be inserted into magnet retaining means 13 which will effectively interrupt the output signal of cardiomyostimulator 8.

The belt-like material 15 may be manufactured from any suitable elastic or non-elastic material, but a preferred embodiment utilizes an elastic material which can be adjusted to variously sized abdomens using a variable fastening device 12 as depicted in FIG. 3A, such as a hook and loop design (such as Velcro® a registered trademark of Velcro USA Inc., of Manchester, N.H.) or a belt and buckle design (not shown). Variable fastening devices allow for infinite adjustability so that one size fits all patients.

The magnet 14 may be permanently affixed to the belt-like material 15 (as by insertion into a subsequently sealed pocket as depicted at 13 in FIG. 3 and/or by an adhesive material, not shown). Alternatively, the magnet may be removable from the belt-like material 15 by any means known in the art, including but not limited to, resealable pockets, adhesives or a Velcro attachment design. Where the magnet is removable, and where the belt-like material 15 is of a fabric nature, the removal of the magnet will assist in the laundering of the belt-like material. Where the belt-like material 15 is of a fabric nature, and where the magnet is not removable, the magnet may be manufactured from or coated with rust retardant materials for laundering purposes.

Referring now to FIG. 3B, there is shown another embodiment of magnetic belt 11 of the present invention including a bar magnet 14a, removably mounted in magnet retaining means which comprises a pouch or pocket 13a having a resealable closure 13b on elastic belt-like material 15, closed with a hook and loop type fastener 12a.

Figure 5:
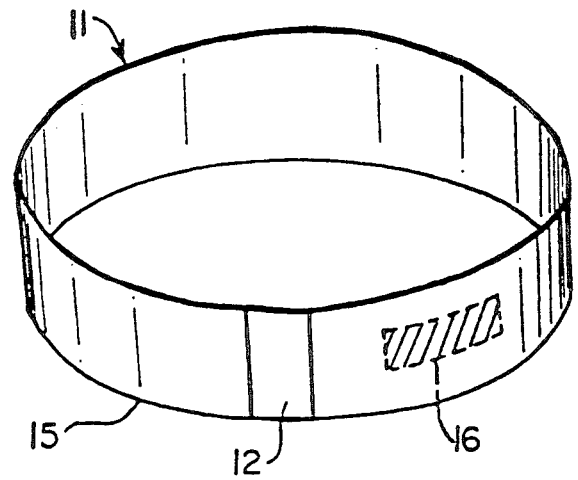
FIG. 5 is a perspective view of the magnetic belt of the present invention showing the use of a magnetic bunting material in a localized position on the magnetic belt.

In another embodiment of the magnetic belt 11 of the present invention, as depicted in FIG. 4, an adjustable belt-like material 15 is designed with flexible magnetic strip or sheet material 16, which is affixed to said belt-like material 15 around the entire circumference of belt-like material 15. As with the previous embodiment, the flexible magnetic strip or sheet material 16 may be permanently or removably affixed to the belt-like material 15. Where flexible magnetic strip or sheet material is utilized, the magnetic strip or sheet material 16 may alternatively comprise either a section of the belt-like material, such as a patch or square area as depicted in FIG. 5. In a preferred embodiment, magnetic strip material 16 is utilized over the entire circumference of the belt-like material 15 so that despite movement by the patient and/or "travel" of the belt-like material 15, the magnetic field remains over that portion of the abdomen wherein the cardiomyostimulator is implanted. Where magnetic strip or sheet material is utilized, it is characterized in that it produces a sufficiently strong magnetic field so as to interrupt the output of the cardiomyostimulator when the belt-like material containing the magnetic sheet material is worn by the patient, while retaining sufficient pliability and durability to withstand normal wearing and laundering operations. This means that there is not one set, predetermined intensity of field strength, and that a range of field strengths will be necessary to vary with the conditions as set out above, including but not limited to the amount of clothing worn by the patient, the amount of fat or other dielectric layers between the cardiomyostimulator and the magnetic sheet material, and the sensitivity of the cardiomyostimulator to magnetic interruption of its output signal. Therefore, it is envisioned with the present invention, that multiple belts 11 will be designed with either permanently affixed magnetic strip material of differing field strengths, or a single belt 11 may be designed with removable magnetic strip material 16, such that magnetic strip material of differing intensities may be inserted for varying conditions. Magnetic strip or sheet material compatible with the present invention includes magnetic bunting material such as Part Numbers MA1280 to MA1720 which are available from Bunting Magnetic Co., of Newton, Kans., and all flexible magnetic strip and sheet materials that achieve a similar result.

Figure 6:
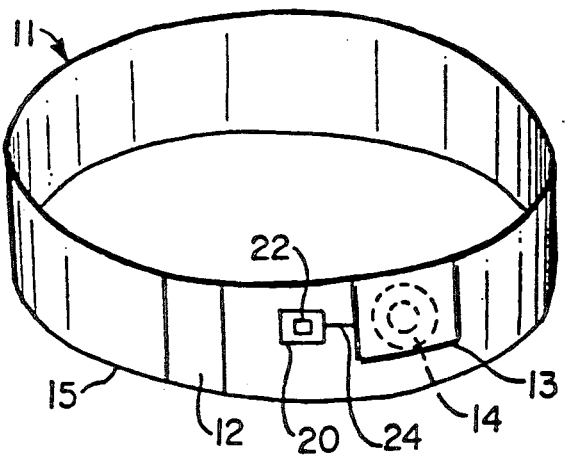
FIG. 6 is a perspective view of the magnetic belt of the present invention showing a switch to control the magnetic output of magnetic material in a localized position on the magnetic belt.

In still another embodiment of the present invention, as depicted in FIG. 6, magnetic belt 11 (utilizing any of the previously described magnetic sources incorporated into magnetic belt 11 by any of the previously described embodiments, although depicted as utilizing pocket 13 and circular magnet 14 shown in phantom, for purposes of illustration), further comprises a device 20 shown diagrammatically, which is associated with magnet 14 by any suitable connection known in the art as shown at 24, wherein device 20 is capable of controlling the magnetic output of magnet 14. Device 20 may include, but is not limited to, an electromagnetic field control mechanism. Device 20 may further include switch 22, which permits the patient to control the magnetic output of magnet 14 simply by manipulating switch 21.

The physical size of the device of the present invention is limited only by the comfort of the wearer. In a preferred embodiment, the belt 11 is approximately six inches wide or less. As indicated previously, the exact length of the belt is not critical as it is envisioned that a variable fastening device 12 will be used to adjust the length to variously sized abdomens.

The belt of the present invention can be worn over clothing or next to the skin, and is worn during prescribed periods for programmed rest, or is applied for safety in emergency situations (under physician defined conditions relative to a specific patient) or during periods of clinical evaluation of the patient's heart function. The belt 11 is removed at all other times when the cardiomyostimulator is to be active, except for those belts that are equipped with a switching device as described above, which may be worn continuously.

While the method of using the device of the present invention must necessarily be tailored to the needs of any individual patient, a general method of use is as follows.

For the first ten days postoperatively, it is suggested that the cardiomyostimulator generate no pulse in order to permit the muscle flap to heal after translocation. After that ten day period, the following training period is suggested beginning with day one of the training period:

| EXAMPLE TRAINING SCHEDULE | |
| --- | --- |
| DAY(S) OF TRAINING PERIOD | DAILY AMOUNT OF STIMULUS |
| Days 1 to 5 | 2 hrs. of stimulus × twice daily = 4 hrs. daily |
| 6 to 10 | 3 hrs. of stimulus × twice daily = 6 |
| 11 to 14 | 4 hrs. of stimulus × twice daily = 8 |
| 14 to 21 | = 8 |
| 21 to 28 | = 12 |
| 28 to 35 | = 18 |
| 35 to 42 | = 24 |
| 42 | Training Period Complete |

With the method of the present invention, the patient wears the device of the present invention for all periods except when it is desired that the muscle flap be stimulated.

The advantages of the present invention are numerous. First, the desired pattern of rest and stimulus is easily achieved both at a specialty care facility and away from a specialty care facility. As indicated above, the stimulation device implanted in patients during the cardiomyoplasty procedure must be turned off from time to time. The advantage of the device of the present invention is that the stimulator does not need to be reprogrammed—it is stopped only during the period in which the belt is worn and it returns to its preprogrammed function when the belt is removed.

Second, the muscle flap may be stimulated for predetermined periods very shortly after surgery with a sufficiently strong pulse so as to cause contraction eliminating the need for an "Increasing Strength/Constantly Pulsed Stimulus Method" to tone or condition the muscle flap. The result is that the muscle is toned at a faster rate with less chance of atrophy.

Third, whether the "full strength/patterned episodes of pulsed stimulus and rest" method is utilized, or the "increasing strength/constantly pulsed stimulus" method is utilized, or a combination of both is utilized, the device of the present invention will work with all methods during incidents of questionable functioning of the stimulator, questionable response from the muscular flap or for evaluation of the patient's own heart or heart function such as by electro- or echo- cardiograms.

Fourth, with the device of the present invention, the patient may be released from the specialized health care facility at a much earlier time and remain away from the specialized health care facility for much longer periods of time, than would otherwise be possible, resulting in far less inconvenience to the patient and in reduced health care costs.

Fifth, during emergency periods, the patient or another attending physician has the ability to control and interrupt the pulse generated by the cardiomyostimulator until the emergency can be effectively analyzed and controlled.

Sixth, the patient has the psychological benefit that accompanies the device and method to control the cardiomyostimulator instantly from any location in the world, during periods of questionable functioning when the skilled physician is not physically present and can render only his or her advice.

The device of the present invention would have an almost unlimited useful life span. A warning label should accompany this device fastened to its body as well as imprinted in all packaging materials, with the words: "Caution Do Not Use In Connection With Cardiac Pacemakers Or Without Supervision Of A Qualified Physician", or other words to that effect.

Having described the invention, it is to be understood that it is not limited to this precise device and method for using the same, and that changes may be made therein without departing from the scope of the invention which is defined in the appended claims.

I claim:

1. A method for use with the cardiomyoplasty surgical procedure to permit patient control of the simulation and conditioning of a translocated muscle flap outside of the confines of a health care facility comprising:
    a) performing the cardiomyoplasty surgical procedure on a patient;
    b) implanting a cardiomyostimulator in the abdomen of said patient as part of said cardiomyoplasty surgical procedure, wherein said cardiomyostimulator provides a continuous output signal of patterned episodes of pulsed stimuli and wherein said cardiomyostimulator includes a means for interrupting said output signal in the presence of a magnetic field;
    c) stimulating said muscle flap with said output signal;
    d) interrupting, by said patient as said patient desires or requires, said stimulation of said muscle flap by interrupting said output signal by associating a magnet over the external surface of said abdomen with a means for removably securing said magnet over said external surface of said abdomen in close proximity to said cardiomyostimulator, said magnet having a field strength of sufficient intensity to interrupt said output signal generated by said cardiomyostimulator so long as said magnet is maintained in close proximity to said cardiomyostimulator;
    e) resuming, by said patient as said patient desires or requires, said stimulation of said muscle flap by resuming said output signal by disassociating said magnet from said surface of said abdomen and said close proximity to said cardiomyostimulator and;
    f) controlling said stimulation and conditioning of said muscle flap by said patient by repeating steps (d)-(e) as said patient requires or desires.

2. The method as defined by claim 1, wherein said magnet of said interrupting step is a bar magnet.

3. The method as defined by claim 2, wherein said magnet of said interrupting step has a limited field strength of only sufficient intensity to interrupt said output signal of said cardiomyostimulator.

4. The method as defined by claim 2, wherein said magnet of said interrupting step has a field strength of approximately 90 gauss measured at 1.5 inches from the magnet surface.

5. The method as defined by claim 2, wherein said magnet of said interrupting step has a field strength of at least 15 pounds per foot pull strength measured on bare metal at zero air gap regardless of magnetization pattern.

6. The method of claim 2, wherein said magnet is a circular magnet or doughnut magnet.

7. The method of claim 2, wherein said magnet is of a strip design.

8. The method of claim 7, wherein said means for removably securing said magnet over said abdomen is a generally belt-like member having a circumference.

9. The method of claim 8, wherein said magnet is incorporated over the entire circumference of said belt-like member.

10. The method of claim 8, wherein said magnet is incorporated over a portion of the circumference of said belt-like member.

11. The method of claim 2, wherein said magnet is a sheet member.

12. The method of claim 11, wherein said means for removably securing said magnet over said abdomen is of a generally belt-like member having a circumference.

13. The method of claim 12, wherein said magnet is incorporated over the entire circumference of said belt-like member.

14. The method of claim 12, wherein said magnet is incorporated over a portion of the circumference of said belt-like.

15. The method of claim 2, wherein said magnet is permanently affixed to said means for removably securing said magnet over said abdomen.

16. The method of claim 15, wherein said means for removably securing said magnet over said abdomen is a belt-like member having a circumference and wherein said magnet is affixed to said means by being permanently incorporated in said belt-like member over the entire circumference of said belt-like member.

17. The method of claim 15, wherein said means for removably securing said magnet over said abdomen is a belt-like member having a circumference and wherein said magnet is affixed to said means by being permanently incorporated in said belt-like member over a portion of the circumference of said belt-like member.

18. The method of claim 15 wherein said means for removably securing said magnet over said abdomen is a belt-like member having a circumference and wherein said magnet is permanently affixed to said means by being permanently enclosed in a pouch permanently affixed to said means.

19. The method as defined by claim 2, wherein said magnet of said interrupting step is not permanently affixed to said means for removably securing said magnet over said abdomen.

20. The method of claim 19, wherein said means for removably securing said magnet over said abdomen is a belt-like member and wherein said magnet is removably incorporated in said belt-like member over the entire circumference of said belt-like member.

21. The method of claim 19, wherein said means for removably securing said magnet over said abdomen is a belt-like member and wherein said magnet is removably incorporated in said belt-like member over a portion of the circumference of said belt-like member.

22. The method of claim 19, wherein said means for removably securing said magnet over said abdomen is a belt-like member and said magnet is removably enclosed in a pouchbeing either permanently or removably affixed to said means.

23. The method of claim 19, wherein said means for removably securing said magnet over said abdomen is a belt-like member and wherein said magnet is permanently enclosed in a pouchbeing removably affixed to said means.

24. The method as defined by claim 19, wherein said means for removably securing said magnet over said abdomen of said interrupting step is belt-like and is composed of non-elastic material.

25. The method as defined by claim 24, wherein said means for removably securing said magnet over said abdomen of said interrupting step includes a variable fastener.

26. The method as defined by claim 25, wherein said means for removably securing said magnet over said abdomen of said interrupting step includes a hook and loop variable fastener.

27. The method of claim 25, wherein said variable fastening means is a buckle.

28. The method as defined by claim 19, wherein said means for removably securing said magnet over said abdomen of said interrupting step is belt-like and is composed of an elastic material.

29. The method as defined by claim 28, wherein said means for removably securing said magnet over said abdomen of said interrupting step includes a variable fastener.

30. The method as defined by claim 29, wherein said means for removably securing said magnet over said abdomen of said interrupting step includes a hook and loop variable fastener.

31. The method as defined by claim 30, wherein said magnet of said interrupting step is removably contained within a resealable pocket integrally formed as part of said means for removably securing said magnet over said abdomen.

32. The method of claim 29, wherein said variable fastening means is a buckle.

33. The method of claim 2, which further comprises: an electromagnetic control device; and a switching means; wherein said switching means activates or deactivates said electromagnetic control device, said electromagnetic control device in turn activates or deactivates the magnetic output from said magnet.

34. The method as defined by claim 1, which comprises the further step of repeating steps (d)–(e), according to a prescribed pattern of rest and stimulus in order to efficiently condition said muscle flap stimulated with said cardiomyostimulator.

* * * * *